United States Patent [19]

Fuller

[11] Patent Number: 4,981,148
[45] Date of Patent: Jan. 1, 1991

[54] BACK TRACTION DEVICE AND METHOD OF USING SAME

[75] Inventor: Ernest Fuller, Walled Lake, Mich.

[73] Assignee: Life Support, Inc., Walled Lake, Mich.

[21] Appl. No.: 354,892

[22] Filed: May 22, 1989

Related U.S. Application Data

[63] Continuation-in-part of Ser. No. 314,970, Feb. 24, 1989, Pat. No. 4,898,185.

[51] Int. Cl.$^5$ ................................................ A61F 5/37
[52] U.S. Cl. ............................ 128/876; 128/DIG. 15; 128/101.1; 128/898
[58] Field of Search ............... 128/873, 874, 875, 876, 128/870, 869, 846, DIG. 15, 101.1; 5/448, 449, 458, 453

[56] References Cited

U.S. PATENT DOCUMENTS

| | | | |
|---|---|---|---|
| 795,108 | 7/1905 | Doellinger | 5/454 X |
| 3,042,940 | 7/1962 | Keaton | 5/449 |
| 4,190,286 | 2/1980 | Bentley | 297/284 |
| 4,286,588 | 9/1981 | Lovegrove | 128/877 |
| 4,444,430 | 4/1984 | Yoshida et al. | 297/284 |
| 4,487,201 | 12/1984 | Ciambarella et al. | 128/876 |

Primary Examiner—Robert A. Hafer
Assistant Examiner—Lynda M. Cofsky
Attorney, Agent, or Firm—Dykema Gossett

[57] ABSTRACT

A back traction device is disclosed that allows a person to be seated in any type of seat and will relieve the pressure, weight and tension on the disc of the lower back of the patient as much as possible. The back traction device consists of a halter that serves to transfer some of the pressure that is associated with sitting in a seat or chair off of the patient's lower back. The back traction device further includes a two-part traction member having a clip-like portion to be received over the back of the seat and a downwardly extending strap portion to be connected to the clip portion. The clip portion is first affixed to the seat back and the strap portion connected thereto. The strap portion has a securing surface that will attach to a corresponding securing surface on the halter member. An inflated air cushion is disposed between the seat occupant and the seat prior to connection of the halter to the strap portion. Since the air cushion is inflated it lifts the seat occupant off the seat at which time the halter is connected to the strap portion. Once the halter has been connected to the strap portion, the air cushion is slowly deflated and the pressure and weight of the seat occupants upper body is transferred through the halter, to the strap portion, and therethrough to the seat. Optionally, a padded back portion may also be attached to provide further support and proper curvature to the patient's lower back.

4 Claims, 2 Drawing Sheets

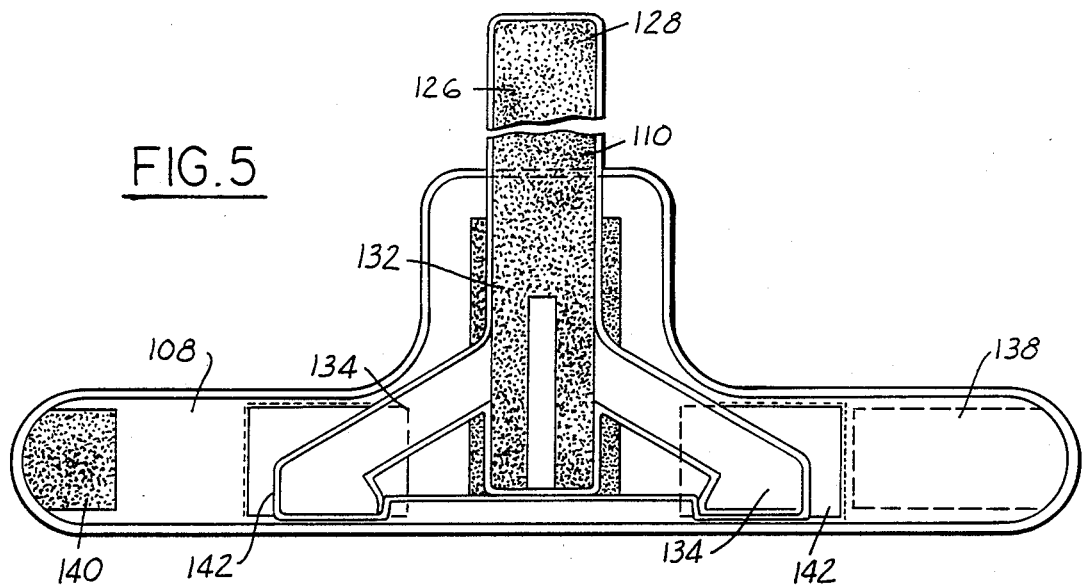
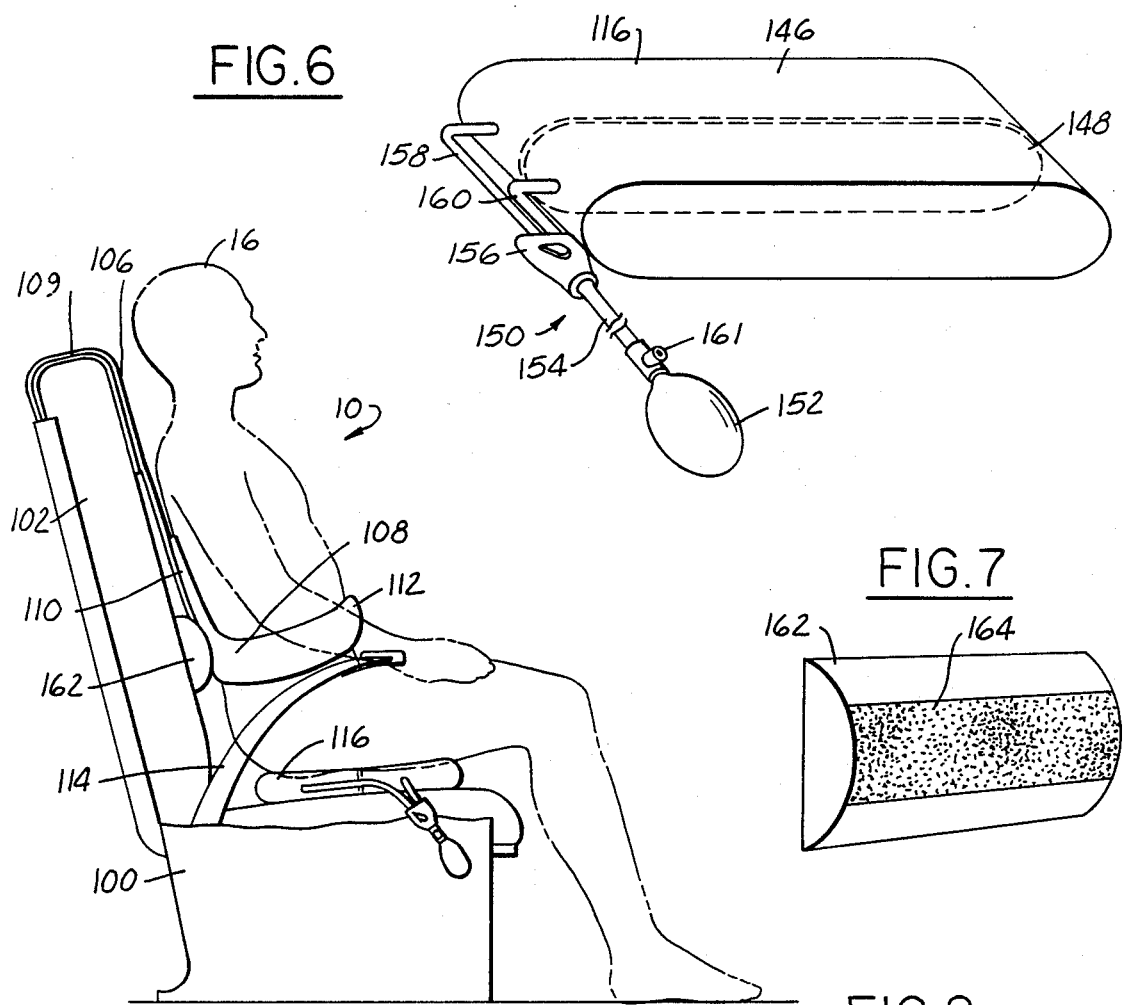
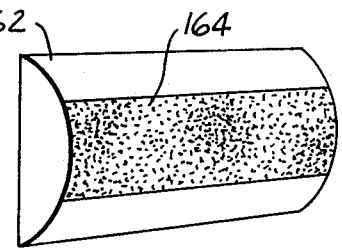

BACK TRACTION DEVICE AND METHOD OF USING SAME

BACKGROUND OF THE INVENTION

This application is a continuation-in-part of U.S. patent application Ser. No. 07/314,970, filed Feb. 24, 1989, now U.S. Pat. No. 4,898,185 the contents of which are expressly incorporated by reference.

This invention in general relates to a back traction device and more particularly to such a device including a halter member adapted to be worn by a person and a traction member adapted to be fitted to a seat, such as an automobile or airline seat. This traction device will provide traction to and reduce the pressure on the disc of the lower back, when the two members are adjustably secured together, with the patient or person seated in the seat. This results in a reduction of the pain in the lower back.

In the past several years, the medical literature has commented on various aspects regarding back injuries. Many of the authorities in the field suggest that a patient should not lay down for extended periods of time after a severe back injury, but instead should begin resuming normal activities as soon as possible. Of course, these normal activities would include such things as sitting in a chair.

Other articles in the medical literature have studied the effect of various postures upon a patient's back. It has been determined that a seating position increases the pressure on a person's lower back by a factor of as much as 140% to 200% of body weight. It has been determined that it is important that a back injury patient have very good support and thereby decrease the pressure in the disc of the lower back as much as possible when using a seat of any type. The medical literature suggested the use of various types of seats with adjustable backs that will conform to and support a patient's back properly.

To actually achieve the above-stated goals has been difficult in practice since a patient might be exposed to several types of chairs in any one day. Even a better or properly fitted chair results in an increase in the pressure in the disc of the lower back as much as 140%. The patient may be utilizing an automobile seat, an airplane seat, or any type of office chair. It is impractical for all of these types of chairs to be adjustable to the individual's back.

Back braces, or thoracic halters, are known that transfer some of the pressure from the disc to other structure in a patient's back. This type of thoracic halter is fitted around the patient to secure and stabilize him. However, such devices, while relieving tension or pressure from the disc of the lower back, do not solve the overall problem.

It would be desirable to transfer or decrease some of the pressure that is associated with sitting to allow the seat to carry the load when the patient is seated in the seat rather than the "other structure" in a patient's back.

It would also be desirable for the traction device to be used by a person with any seat, including an automobile seat, an airline seat or the like in which the individual sits.

It is therefore an object of this invention to provide a back traction device that has a thoracic halter worn by a user and a traction member mounted on the back of a seat whereby, when the user is seated, the pressure in the disc of the lower back is transferred to the seat, relieving the patient or user's lower back pain.

It is further an object of this invention to provide such a back traction device that may be adapted for use with any type of seat or any type of waist-worn halter construction.

Moreover, it is an object of the present invention to provide such a back traction device including a combination halter member and traction member that is relatively simple to manufacture and utilize.

SUMMARY OF THE INVENTION

The invention consists of a combination of a traction member and a back halter member, wherein both the traction member and the back halter member have mating securing surfaces formed thereon. The halter member is fitted around the user or patient, the traction member is attached to a seat, and the patient or user then is seated in the seat. The mating securing surfaces on the traction member and the halter or halter member are engaged, and the pressure or weight from the upper body of the wearer is transferred from the halter to the seat through the back traction device.

The traction member of the back traction device may be fitted to any type of seat and is adapted so as to be easily fitted over airline seats or the like.

A preferred embodiment of the present invention consists of a halter or halter member that has an elongate central portion and two elongate wing portions that wrap around the patient's waist. The wing portions are formed with mating securing surfaces that secure the halter to the patient. The elongate central portion is formed with a securing surface on the rear thereof. The securing surface on the rear of the elongate central portion of the halter is mounted to the seat, preferably around the waist to support the ribs and upper body weight from the halter, thus better transferring the weight from the halter to the seat. The securing surfaces are preferably formed of hook and loop type material fastening means or straps. Hook and loop type materials sold under the trademark Velcro TM are representative of the type of fasteners which are preferably used.

The traction member in a preferred embodiment consists of a sheet of hook and loop type material that will mate with the hook and type material means attached to the back of the halter. The traction member of this invention is a two-piece item having a first clip-like portion that is received over the top of a seat back, such as an airline seat. The clip portion has a securing surface on an outer portion thereof. A second strap portion has a securing surface on both faces, one of which is received upon the clip portion to secure the strap portion to the clip portion. The other securing face of the strap portion is attached to the securing surface on the halter.

An air inflated seat cushion and a pump therefore is disclosed that is used to lift the seat occupant above the normal height of the seat portion of the seat prior to attachment of the halter to the traction member. In this way, it is assured that the pressure from the upper body of the wearer will be transferred from the halter to the seat through the traction member. That is, since the person will be lifted above the seat when the halter is attached to the strap portion of the traction member, the pressure and weight will be supported by the traction member. The air seat cushion is then slowly deflated.

Optionally, a back padded device may also be attached to either the securing surface on the strap portion.

These and other features and objects of the present invention can be best understood upon study of the attached specification and drawings, of which the following is a brief description thereof.

BRIEF DESCRIPTION OF THE DRAWINGS

FIG. 5 is a view similar to FIG. 4 but showing the reverse side of the connection of the traction device to the back halter.

FIG. 6 shows a air inflated cushion and a pump for temporary support of the seat occupant above the height of the seat.

FIG. 7 shows an optional back padded device.

FIG. 8 is a cross-sectional view through an airline seat showing the combination of the halter and traction device of the present invention in use with the optional back padded device.

DETAILED DESCRIPTION OF THE PREFERRED EMBODIMENT

Figure 1:
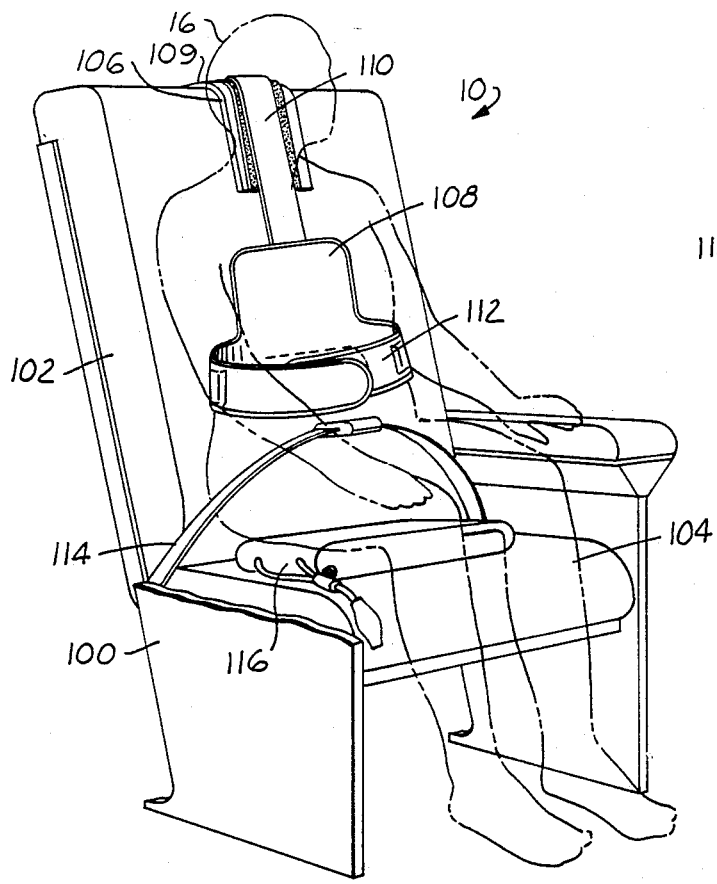
FIG. 1 is a perspective view showing the combination of a halter and traction member attached to an airline seat with a seat occupant shown in phantom.

As shown in FIG. 1, the back traction device assembly 10, consists of a thoracic halter 108 and a traction member 106 that consists of a first clip-like portion 109 and a second strap-like portion 110. The halter 108 is shown fitted around a seat occupant 16 by a belt portion 112. The first clip-like portion 109 is received upon the top of the back 102 of an airline seat 100. Strap portion 110 is attached to the clip portion 109 and the halter 108 is attached to strap portion 110. The seat occupant 16 sits on the seat portion 104 of the airline seat 100 and an inflatable bag or cushion 116 is illustrated as underneath the seat occupant 16.

Figure 2:
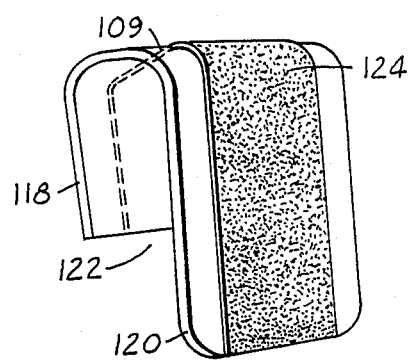
FIG. 2 shows a first clip portion of the traction device of the present invention.

FIG. 2 shows the clip portion 109 of the traction member 106. Clip portion 109 consists of a first extending portion 118 and a second extending portion 120. The two extending portions extend in the same direction so as to create an intermediate portion 122 that results in a generally J-shaped clip member. A securing surface 124, that may be Velcro TM, is formed at an outer surface of the clip portion 109.

Figure 3:
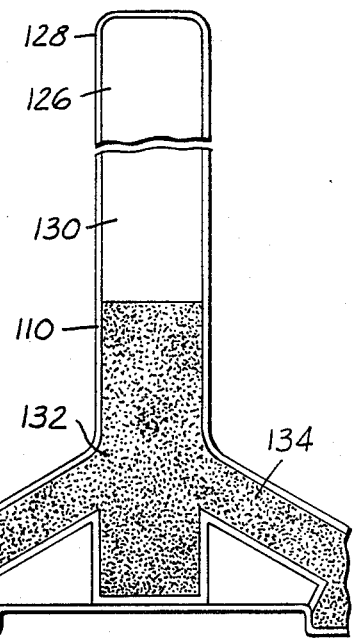
FIG. 3 shows a second strap portion of the traction device of the present invention.

FIG. 3 shows the strap portion 110 of the traction member 106 of the present invention. Strap portion 110 consists of an upper portion 126 that is illustrated as being free from any securing surface on a first face 130. A second face 128, not illustrated in FIG. 3 is defined as the face opposed from face 130. The lower portion of strap portion 110 consists of a central portion 132 and two wing-like portions 134 extending from the central portion 132. Central portions 132 and wings 134 are all covered with a securing surface on face 130.

Figure 4:
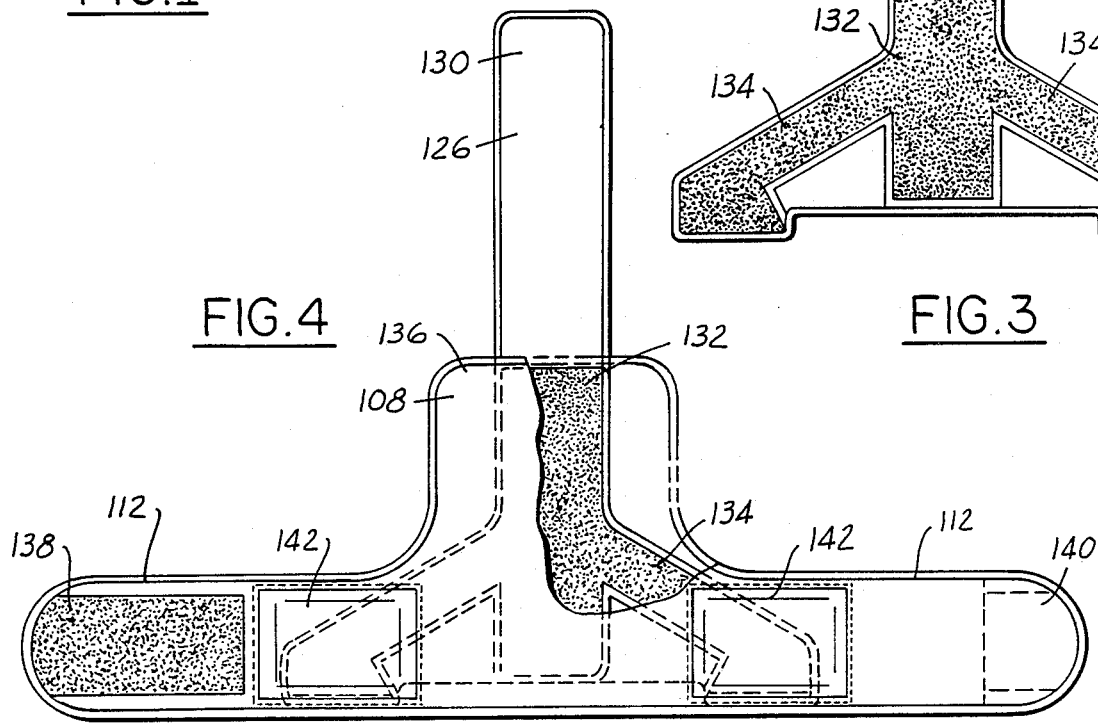
FIG. 4 shows the connection of the second portion of the traction device of the present invention to a back halter member.

As shown in FIG. 4, strap portion 110 may be connected to halter 108 along the securing surfaces on the two members. Central portion 132 is connected to a central portion 136 of halter 108. Wings 134 are each connected to securing surfaces 142 formed on halter 108. The securing surfaces on the central portion 136 and surfaces 142 of the halter are not illustrated in FIG. 4, however, it is to be understood they correspond to the securing surfaces on the central portion 132 and wings 134 of strap portion 110. As can also be seen from FIG. 4, the belt portion 112 of the halter 108 consists of a first belt-like portion 138 having a securing surface on one face and the second belt-like portion 140 having a corresponding securing surface on an opposed face. Thus, the belt-like portions 138, 140 can be wrapped around a seat occupant and secured at the securing surfaces. In a preferred embodiment, the securing surfaces are covered with Velcro TM and thus can be adjusted to conform to the size of various seat occupants.

FIG. 5 shows the combination of strap portion 110 and halter 108 from the reverse side than that illustrated in FIG. 4. As can be seen in FIG. 5, the second face 128 of strap portion 110 has a securing surface on the upper portion 126. Additionally, lower central portion 132 is also shown to have a securing surface on the rear face thereof. Wings 134 are shown to be free from any securing surface at the rear face 128. As is also clear from FIG. 5 second belt-like portion 140 has a securing surface on the opposed side to correspond to the belt-like portion 138.

The strap 110 is thus connected to the halter 108 at a position corresponding to the patient's waist. In this way, the transfer of pressure to the seat 100 is assured.

Inflatable air cushion 116 is illustrated in FIG. 7. The inflatable cushion 116 is shown to comprise two sections 146 and 148 each of which are inflated by a pump combination 150. Pump combination 150 has a bulb 152 that may be manually squeezed to pump air through tube 154, to a Y-connector 156 and through tubes 158, 162 to sections 146 and 148. By squeezing bulb 152 the sections 146 and 148 can both be filled. A valve 161 is disposed on pump combination 150 to allow deflation of sections 146 and 148 when that is desired by the seat occupant 16. Pump combination 150 is of a well-known type.

FIG. 7 shows an optional back padded device 162 that has a securing strap 164 formed at an outer surface thereof. As can be seen, back padded device 162 is curved outwardly to provide support to the lower back of the seat occupant 16.

FIG. 8 shows the combination of the halter 108, traction member 106 and the optional back padded device 162 mounted upon an airline seat 100. As is shown in FIG. 8, seat occupant 16 is received within airline seat 100 and has a seat belt 114 attaching him thereto. Halter 108 is connected by belt portion 112 to the seat occupant 16. Traction member 106 is attached to the airline seat 100 through clip portion 109 which is shown clipped over the back 102 of airline seat 100. Strap portion 110 is shown downwardly extending from clip portion 109 and is shown attached to halter 108. Optional back padded portion 162 is shown at a position corresponding to the lower back of seat occupant 16. The securing surface 164 on optional back padded portion 162 is secured to the corresponding securing surface on the lower central portion 132 of the strap portion 110. Inflatable air cushion 116 is shown received beneath the seat occupant 16.

Since the securing surfaces allow the various member to be secured at a variety of positions, the position of the seat occupant 16 with respect to the traction member can be adjusted to accommodate various heights of seat occupants. In addition, the same adjustability of position applies to the optional back padded device 162. Air cushion 116 allows the seat occupant to be positioned upwardly so as to allow some further accommodation for various heights of seat occupants.

In use, the seat occupant will first place the clip-like portion 109 above the back 102 of the airline seat 100. Strap portion 110 is then attached to clip portion 109 and allowed to extend downwardly. The seat occupant 16 then places the inflatable air cushion 116 upon the seat portion 104 of the airline seat 100. The cushion can then be inflated. The occupant will then be seated and is raised off the seat portion 104 of the seat. Once seat occupant 16 has been supported above the seat portion 104 of seat 100 the halter 108 may be connected to the strap portion 110. If the optional back padded portion 162 is to be utilized, it should be attached to the strap portion 110 prior to this attachment to the halter 108.

Once the halter 108 is attached to strap portion 110, the air within air cushion 116 is slowly released and the seat occupant is allowed to move gradually back downwardly upon seat portion 104 of airline seat 100. However, since the halter 108 has been attached to the strap portion 110 at a position with the seat occupant 16 raised above seat portion 104, the pressure and weight will be transferred from halter 108 to strap portion 110. The occupant releases air through valve 161. The occupant can completely deflate the cushion 116 or only partially deflate it, depending on which is most comfortable.

The lateral extent of clip portion 109 is made small enough such that it can fit between the support bars of a seat headrest. This facilitates the use of traction member 106 with any type of automobile seat.

A preferred embodiment of the present invention has been disclosed; however, certain modifications will be obvious to one of ordinary skill in the art. The intended scope of the invention can be best understood upon the reading of the appended claims.

I claim:

1. A method of supporting the weight of the seat occupant in a seat comprising the steps of:
   (a) attaching a traction member to a seat;
   (b) attaching a halter to a seat occupant;
   (c) placing an inflatable air bag upon a seat to be occupied by the seat occupant; and
   (d) inflating the air bag, seating the seat occupant in the seat, attaching the halter to the traction member, and deflating the air bag thus allowing the seat occupant to return towards a normal sitting position upon the seat.

2. A method as recited in claim 1, and further wherein the deflation of the air bag being gradual to allow a seat occupant to slowly adjust a sitting position with respect to the traction member.

3. A method as recited in claim 2, and further wherein the air bag is not totally deflated upon final positioning of the seat occupant.

4. A method as recited in claim 1, and wherein the attachment of the halter to the seat occupant and the attachment of the halter to the traction member both utilize hook and loop type material securing surfaces.

* * * * *